United States Patent [19]

Adams et al.

[11] Patent Number: 5,334,529
[45] Date of Patent: Aug. 2, 1994

[54] STABLY TRANSFORMED COFFEE PLANT CELLS AND PLANTLETS

[75] Inventors: Tommy L. Adams, Millbrae; Michael A. Zarowitz, San Carlos, both of Calif.

[73] Assignee: Escagenetics Corporation, San Carlos, Calif.

[21] Appl. No.: 988,009

[22] Filed: Dec. 10, 1992

Related U.S. Application Data

[63] Continuation of Ser. No. 726,579, Aug. 12, 1991, abandoned, which is a continuation of Ser. No. 373,021, Jun. 27, 1989, abandoned.

[51] Int. Cl.$^5$ .............................................. C12N 5/14
[52] U.S. Cl. ........................ 435/240.4; 435/240.47; 435/240.49; 800/205; 935/67
[58] Field of Search ........... 435/240.4, 240.47, 240.49; 800/205, DIG. 65, 250; 935/67

[56] References Cited

PUBLICATIONS

Potrykus et al in *Plant Gene Research: Plant DNA Infectious Agents*, Springer-Verlag, 1987, p. 240.
Gelvin (1987) Plant Molecular Biology 8: 355–359.
Schöpke et al (1987) Plant Cell, Tissue and Organ Culture 8: 243–248.
Orozco et al. (1984) Turrialba 34: 534–536.
Fromm et al. (1985) Proc. Natl. Acad. Sci., U.S.A. 82: 5824–5828.
Orozco, et al (1983) 6th International Protoplast Symposium, Poster Proceedings, Birkhauser Verlag, pp. 52–53.

*Primary Examiner*—Che S. Chereskin
*Attorney, Agent, or Firm*—Spensley Horn Jubas & Lubitz

[57] ABSTRACT

Stably transformed *Coffea arabica* plant cells, derived from protoplasts and capable of regeneration, are disclosed.

8 Claims, No Drawings

STABLY TRANSFORMED COFFEE PLANT CELLS AND PLANTLETS

This is a continuation of application Ser. No. 07/726,579 filed on Aug. 12, 1991, now abandoned, which is a continuation of application Ser. No. 07/373,021, filed Jun. 27, 1989, now abandoned.

BACKGROUND OF THE INVENTION

The genus Coffea consists of about 70 species of which *C. arabica* is the most economically important. This species accounts for about 70% of the estimated $15 billion annual market. Although other species of Coffea have such potentially desirable genetic traits as, for example, the absence of caffeine production and disease resistance, these species are generally undesirable because of other factors such as low yield of beans or beans which produce a poor quality coffee. While it would be desirable to combine these genetic traits with those of *C. arabica*, traditional plant breeding techniques have been largely unsuccessful since *C. arabica* is tetraploid whereas the other species are diploid. The non-arabica species are also self-incompatible. As a result, the transfer of genetic traits from wild outbred species of the genus to the cultivated *C. arabica* cultivar is quite difficult. A further complication is Coffea's lengthy period for fruit development and the 2–4 year bean-to-bean generation time which make such traditional approaches costly and time consuming.

More recently, interest has turned to in vitro cell culture and recombinant techniques in order to genetically modify members of the genus Coffea. In vitro techniques have been applied to various aspects in the cultivation of coffee. Staritsky (Acta Bot. Neerl., 19:509, 1970 ) induced callus tissues from orthotropic shoots of *C. canephora, C. arabica* and *C. liberica*, but obtained somatic embryos and plantlets only from *C. canephora*. Callus from endosperm tissues of *C. arabica* was induced by Keller, et al. (Planta, 108:339, 1972) for the purpose of studying caffeine synthesis. Sharp, et al. (Phyton, 31:67, 1973) cultured somatic and haploid tissues of *C. arabica* and obtained callus growth (petioles, leaves, green fruits), proembryo formation (anthers) and shoot development (orthotropic shoots). For the purpose of producing coffee aroma from suspension cultures, Townsley (Can. Inst. Food Sci. Technol., 7:79, 1974) established liquid cultures of coffee cells from friable callus derived from orthotropic shoots of *C. arabica*. The distinction of high and low frequencies of somatic embryo induction from cultured mature leaf explants of *C. arabica* (cultivar Bourbon) were described by Sondahl, et al. (Abstract, International Conference on Regulation of Developmental Processes in Plants, Halle, 180, 1977). In addition, protoplasts have been isolated from leaf-derived callus tissues of *C. arabica* (cultivar Bourbon) and callus regeneration was obtained in about 30% of the cultures (Staritsky, Acta Bot. Neerl., 19:509, 1970). However, no plant regeneration from these calli were reported. More recently, Schopke, et al., ( Plant Cell, Tissue and Organ Culture, 8:243, 1987) reported the somatic embryogenesis and regeneration of plantlets in protoplast cultures from somatic embryos of *C. canephora*.

Although considerable research has been done to asexually modify the genetic composition of the various species of Coffea, to date attempts to regenerate stable genetically modified whole plants from protoplasts have been unsuccessful. Thus, there is considerable need for plants of the genus Coffea which are genetically modified and stable such that the genetic modification is transmitted to progeny.

SUMMARY OF THE INVENTION

The present invention arose out of the discovery that a genetically modified protoplast of the genus Coffea could be produced from which a whole plant can be regenerated which stably incorporates a genetic change induced in the protoplast. A means for introducing DNA which genetically modifies such a protoplast is electroporation.

Accordingly, the present invention relates to (1) genetically modified protoplasts of the genus Coffea from which whole plants can be regenerated, (2) plants regenerated from these protoplasts which stably incorporate a genetic change induced in the protoplasts, (3) seeds produced by these plants or their progeny, and (4) tissue derived from these plants or their progeny. The present invention utilizes cell culture technology to isolate, charactarize, and develop genetically modified protoplasts which genetically transmit a genetic modification to their progeny.

Various other objects, features and attendant advantages of the present invention will be more fully appreciated as the same becomes better understood from the following detailed description in connection with the accompanying examples.

DETAILED DESCRIPTION OF THE INVENTION

The invention comprises at its most fundamental level a genetically modified protoplast of the genus Coffea which can be used to regenerate a whole plant which stably retains the genetic modification. In turn, the seed produced by this plant carries the genetic modification such that plants generated from the germination and outgrowth of the seed also retain the stable genetic modification. Thus, the progeny can transmit the stable genetic modification to future generations of Coffea.

In the embodiment illustrated herein, protoplasts of the genus Coffea were produced which were genetically modified with the gene for kanamycin resistance. Surprisingly, these protoplasts can be regenerated to cells and whole plants in which the kanamycin gene is stably present. This represents the first known instance where whole plants of the genus Coffea containing a stable foreign genetic trait can be regenerated from genetically modified protoplasts. As a consequence of this genetic stability, this foreign genetic trait is carried by progeny of the protoplast and plants regenerated therefrom.

The protoplasts of the invention can be genetically modified through mutagenesis or through the introduction of exogenous DNA coding for regulatory or structural genetic functions. This exogenous DNA can be introduced by using an intermediary device (e.g., virus, bacteria, nuclear fusion, DNA-coated particle or orgenelle) or via direct techniques (e.g., PEG, $CaCl_2$, or other DNA condensation techniques, membrane fracture techniques, electroporation, or microinjection).

A wide variety of regulatory and structural genes of prokaryotic or eukaryotic origin along with other DNA, as present in individual chromosomes, nuclei, or DNA constructs may be introduced into the protoplast to become integrated into the plant genome. The DNA may be "bare" or incorporated into a vector system (e.g., systems based on the Ti plasmid or the Caulimoviruses). Structural genes introduced may provide for a wide variety of modifications. By introducing genes which control various functions, the functions of the plant can be widely varied: plant growth can be inhibited or enhanced; nutrient requirements may be modified; production of various plant products can be increased or decreased; and enhanced protein and/or saccharide content can be provided. Also, the plant can be adapted to survive in hostile environments, such as reduced light, lower temperature, or brackish water; protected against microbial and pest infection; and herbicide resistance may be imparted to the cells. These and other modifications can be achieved by providing structural genes which produce the particular proteins responsible for these characteristics or regulatory genes for altering expression.

With respect to the genus Coffea, of particular interest are genetic modifications which alter the purine alkaloid content (e.g., caffeine), increase both agronomic and beverage-related solids (carbohydrates), and increase pest resistance.

In terms of modifying the purine alkaloid content, the biochemical pathway for caffeine synthesis has been partially described for Theobroma (cocoa), Camellia ( tea ), and Coffea (Bauman, et al., in Biotechnology in Agriculture and Forestry, Vol. 4, Medicinal and Aromatic Plants I, Bajaj, ed., Springer-Verlag, Berlin, 1988). Thus, caffeine concentration may be increased by, for example, uncoupling caffeine synthesis from feedback regulation. Alternatively, the preferred method for reducing caffeine concentration is the introduction of genes that block caffeine synthesis de novo rather than genes which degrade caffeine as it is produced (Woolfolk, J. Bact, 123:1088, 1975). The first step, and probably also the branch point in caffeine synthesis is thought to be the methylation of xanthosine to 7-methylxanthosine. Alternatively, caffeine synthesis may be inhibited by producing plants with a regulated copy of a gene which expresses, for example, a ribozyme (Haseloff, et al., Nature, 334:585, 1988) to the mRNA for the methyltransferase gene responsible for the methylation of xanthosine to 7-methylxanthosine or as anti-sense RNA (Ecker, et al., Proc. Natl. Read, Sci. U.S.A., 83:5372, 1986; Smith, et al., Nature, 334:724, 1986).

With respect to beverage related solids, bean carbohydrates make up a significant portion of the extractable solids found in quality extracts of coffee (Amorim, et al., Turrialba, 24(2):214, 1974; Thaler, Fd. Chem., 4:13, 1979; Strobel, in Banbury Report Vol 17, Coffee and Health, MacMahon, et al., eds., Cold Spring Harbor Laboratory, Cold Spring Harbor, N.Y., 1984). Higher extraction rates are possible, but only at the cost of co-extraction of quality-degrading compounds. Higher coffee extract yields that retain good quality can be achieved by increasing the content of the easily extracted bean carbohydrate, which is mostly galactomannans. This may be accomplished by either increasing the gene dosage or altering the gene regulation of gene constructs that are responsible for galactomannan synthesis, or by introducing genes that would produce an additional extractable carbohydrate (e.g., by introduction of an appropriately regulated ADPglucose pyrophosphorylase gene for increased starch synthesis).

The carbohydrates stored in the woody portions of the coffee plant during vegetative growth periods (as opposed to fruiting periods) play an important role in determining the fruiting capacity of the plant (Cannell, et al., Ann. Appl. Biol., 64: 345, 1969; Cannell, Ann. Appl. Biol., 67:99, 1971; Janardhan, et al., Indian Coffee, 35.(4):145, 1971). During the fruiting seasons, this starch storage carbohydrate is depleted and used as an additional carbon source for the developing berries. If there are too many berries for the amount of photosynthesis and storage carbohydrate, the plant is said to be "overbearing" and suffers from berry-drop. The resulting massive depletion of starch from the woody portions of the plant can be so great as to be lethal to the plant. Subject to the photosynthetic capacity of the plant and other factors, it would be possible to increase the amount of starch deposition in the woody tissues during vegetative growth periods by introducing an additional, appropriately regulated, ADPglucose pyrophoshorylase activity into the plant. This would provide more carbon to the berries during the fruiting seasons, and therefore, increase the carrying capacity of the plant.

Also important are genetic modifications which result in increases in pest resistance which can be introduced using genes, for example, for *Bacillus thuringiensis* bt toxin (Vaeck, et al., Nature, 328: 33, 1987 ), cowpea trypsin inhibitor (Bilder, et al., Nature, 330:160, 1987), glyphosate resistance (della-Cioppa, et al., Bio/Technology, 5:579, 1987), bromoxynil resistance (Stalker, et al., Science, 242:413, 1988), phosphinothricine resistance (DeBlock, et al., EMBO J., 6(9):2513, 1987) and vital coat protein cross protection (Register, et al., Virology, 166:524, 1988).

Thus, although one particular technique has been taught herein to genetically modify Coffea protoplasts, a number of equivalent techniques could be used. Throughout the specification, the term "genetically modified" is used to designate asexual genomic changes which can result, for example, from the asexual alteration of the Coffea endogenous genetic repertoire, or by the addition of exogenous DNA, i.e., foreign DNA or DNA from the same or a different variety of Coffea as the variety of the protoplast. These genomic changes may relate to a regulatory or a structural gene.

The alteration of an endogenous genetic function can occur, for example, by mutation. It is well known that mutations can be intentionally produced by a variety of known procedures. For example, mutants can be induced using chemical, radioactive, and recombinant techniques. As shown in Table 1, chemical mutagens can be divided into four main groups based upon their activity.

TABLE 1

| ACTIVITY | EXAMPLES |
|---|---|
| Base Analogs | 5-bromouracil, 2-aminopurine |
| Deaminating Agents | nitrous acid, hydroxylamine |
| Alkylating Agents | ethyl ethanesulfonate, nitrosoguanidine |
| Acridine Derivatives | acridine orange, ethidium bromide |

Radiation induced mutations can be caused by such agents as ultraviolet light, and x-rays. The primary mechanism by which mutations may be caused results from excision or post replication repair by recombination.

Alternatively, genetic modification can be accomplished through transformation. The term "transformation" as used herein is meant to denote a process used for the addition of any DNA to the genomic repertoire of a species or variety of Coffea by means other than the normal methods of sexual reproduction. The term "foreign DNA" denotes DNA derived from a species other than the species being transformed. A wide variety of techniques may be employed for DNA introduction into Coffea such as transformation with $Ca^{++}$ precipitated bare DNA, a plasmid, or a mini-chromosome, where the DNA can be replicated and the structural gene expressed in the host, or introduction into the host as the structural gene and flanking regions by direct insertion, for example, micropipette, whereby the DNA may be integrated into the host genome or is introduced by non-sexual means.

The asexual introduction of isolated genes or a group of genes into the genome of Coffea typically uses an efficient host gene vector system. The exogenous genes should be expressed in the transformed plant cells and stably transmitted (somatically and sexually) to the next generation of cells produced. The vector should be capable of introducing, maintaining, and expressing a gene in Coffea cells, from a variety of sources, including but not limited to plants and animals, bacteria, fungi, yeast or virus. The location of the new gene in the Coffea genome may be important in determining effective gene expression of the transformed plant. In addition, to be effective, the genetic modification must be passed on to progeny by normal breeding.

Directed asexual genetic modification and expression of exogenous genes in dicotyledonous plants has been shown to be possible using the T-DNA of the tumor-inducing (Ti) plasmid of *Agrobacterium tumefaciens*. Using recombinant DNA techniques and bacterial genetics, any exogenous piece of DNA can be inserted into T-DNA in Agrobacterium. Following infection by this bacterium, the exogenous DNA is inserted into the host plant genome, thus producing a genetically engineered cell and eventually a genetically engineered plant. A second approach is to introduce root-inducing (Ri) plasmids as the gene vectors.

Ti-plasmid DNA, or any other free DNA, can also be asexually introduced into Coffea by artificial methods such as microinjection, or fusion between protoplasts and bacterial spheroplasts containing the gene vector which can then be integrated into the Coffea nuclear DNA.

It is believed that genetic engineering of Coffea can also be accomplished by introducing the desired DNA containing the desired functional genes using DNA molecules of a variety of forms and origins including, but not limited to: plant pathogens such as DNA viruses like Cauliflower Mosaic virus (CaMV) or geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components, (e.g., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of Coffea. Particularly of interest are fragments having the replication function and lacking other functions such as oncogenesis, virulence, and so forth ). Transposons may also be used to carry foreign genes into Coffea DNA.

As described above, DNA may be delivered into the protoplasts directly by plasmids, such as Ti, viruses or microorganisms like *A. tumefaciens*. Alternatively, exogenous DNA can be delivered by such non-vector techniques as liposomes, microinjection by mechanical or laser beam methods, by DNA coated particles, by whole chromosomes or chromosome fragments, and by fusion of whole nuclei.

Two transformation methods which can be used to obtain the Coffea protoplasts of the invention are calcium phosphate techniques and electroporation. The calcium phosphate technique produces a chemical environment in which DNA attaches to the surface of the protoplast, after which the DNA is endocytosed by an unknown pathway. Other techniques for DNA uptake which are known include using PEG (Shillito, et al., in Methods in Enzymology, Vol. I53, Part D, Chapter 19, Wu, et al., eds., Academic Press, New York, 1987), PVA (Power, et al., in Methods in Enzymology, Vol. 118, Chapter 41, Weissbach, et al., eds., Academic Press, New York, 1986), and polyamines (Power, et al., ibid).

Electroporation utilizes the fact that the protoplast membrane acts as an electrical capacitor which is generally unable to pass current. Subjecting the protoplast membranes to a high-voltage electric field is believed to result in their temporary breakdown and the formation of pores that are large enough to allow macromolecules to enter or leave the cell. During the time that the pores are open, nucleic acid can enter the cell and ultimately the nucleus. Due to its free ends, linear DNA is more recombinogenic and more likely to be integrated into the host chromosome to yield permanent, or stable, transformed protoplasts.

The transformed Coffea protoplasts of the invention containing the exogenous DNA may be selected either directly or indirectly. With direct selection, the transformed protoplasts are exposed to selective pressure based upon the actual function of the exogenous DNA. For example, if the exogenous DNA codes for excess levels of glutamine synthetase, then protoplasts and cells regenerated from them that have this DNA could be selected by adding phosphinothricin (PPI) to the protoplast growth medium. Since only protoplasts having the glutamine synthetase expressing DNA could survive in the presence of elevated levels of PPT, with time only these protoplasts or cells would be capable of survival.

A preferred isolation technique for indirect selection of the stably transformed Coffea cells is by use of a selectable marker. In this technique the exogenous DNA for the desired transforming trait (e.g., herbicide or pest resistance, increased solids production, or inhibition of caffeine productivity) is transformed along with a gene which expresses a selectable marker. The cells are then allowed to grow in the presence of a selective agent in order to allow only those cells having the selectable marker to proliferate. Using this approach, there is a reasonable likelihood that a certain percentage of the protoplasts which acquired the selectable marker gene also acquired the desired exogenous DNA.

Although it is possible to prepare a genetic construct, such as a plasmid, which contains the genetic sequence of both the selectable marker and the desired trait, it is also possible to stably transform the cells using different genetic constructs for each gene. In this latter case the protoplasts will typically be exposed to a ratio of selectable construct to trait construct which is less than 1

(e.g., 1:5). In some circumstances selection requires transformation of a large amount of selection construct and a high ratio is not practical. In such instances, a single construct with both genes should be used for transformation.

Examples of selectable marker genes and associated selective agents which can be used are described in Kaufman, et al., Proc. Natl. Acad. Sci. U.S.A., 8.3.:3136, 1986 (adenosine deaminase); Southern, et al., J. Mol. Appl. Gen., !:327, 1982 (aminoglycoside phosphotransferase); Simonsen, et al., Proc. Natl. Acad. Sci. U.S.A., 80:2495, 1983 (dihydrofolate reductase); Palmer, et al., Proc. Natl. Acad. Sci. U.S.A.,84:1055, 1987, (hygromycin-B-phosphotransferase); Littlefield, Science, 145:709, 1964 (thymidine kinase) and Mulligan, et al., Proc. Natl. Acad. Sci. U.S.A., 78:2072, 1981 (xanthine-guanine phospho-ribosyltransferase).

Calcium phosphate and PEG transfection, Agrobacterium, as well as electroporation are preferred for producing stable transformants, as all four techniques introduce adequate amounts of DNA into large numbers of plant cells or protoplasts. This, in turn, increases the probability that some cells or protoplasts will stably integrate the exogenous DNA into the genome.

Selections are carried out until cells or tissue are recovered which are growing well in the presence of the selective agent. These "cell lines" are then repeatedly subcultured in the presence of the selective agent and characterized. The amount of resistance to the selective agent which has been obtained is determined by comparing the growth of these cell lines with the growth of unselected cells or tissue in the presence of various concentrations of selective agent. To avoid the selection of habituated cells, stability of the trait of the cultured cells may be evaluated by simply growing the selected cell lines in the absence of the selective agent for various periods of time and then analyzing growth after reexposing the tissue to the selective agent.

Cell lines exhibiting satisfactory levels of resistance to the selective agent are put through a plant regeneration protocol to obtain mature plants and seeds expressing the resistance trait. The plant regeneration protocol allows the development of plantlets. If development is by organogenesis, then shoots are induced from callus and the shoots are then induced to root.

In addition to testing for the selectable marker gene, or its expression product, as described above, the presence of the desired gene in the plant cells can be established in a wide variety of ways, depending on the nature of the gene. The presence of a gene which produces an exogenous product may be detected by isolation and lysis of the plant cell and an analysis of the cytoplasm for the exogenous product, or of the nucleus for the exogenous gene. The exogenous product may be detected by electrophoresis, chromatography, immunoassay, or the like. The gene can be detected conveniently by hybridization (e.g., by using Southern Blotting).

The cells are regenerated into callus tissue by culturing in an aseptic environment using a phytohormone-containing culture medium. Calli are forced via hormone or growth regulator treatments (e.g., cytokinin, auxin, or complete removal of all hormones) to either regenerate directly into plantlets, or to first form somatic embryos and then to germinate into plantlets. The genetically-modified plantlets may then be potted in a sterile potting mix and permitted to grow.

Mature plants are then obtained from cell lines that are known to carry the genetic modification. Preferably, the regenerated plants are self pollinating. Otherwise pollen obtained from the regenerated plants is crossed to seed grown plants of agronomically important inbred lines. Conversely, pollen from plants of these inbred lines is used to pollinate regenerated plants. The genetics of the trait is then characterized by evaluating the segregation of the trait in first and later generation progeny. The heritability and expression in Coffea plants of traits selected in tissue culture are of particular importance if the traits are going to be commercially useful.

The above disclosure generally describes the present invention. A more complete understanding can be obtained by reference to the following specific examples which are provided for purposes of illustration only, and are not intended to be limiting unless otherwise specified.

EXAMPLE 1

Preparation of Coffea Protoplasts which Retain Plant Regeneration Capability

Production of Coffea Callus

Young leaves from *Coffea arabica* plants were surface sterilized by washing in a 1% liquinox solution for five minutes, a 7% calcium hypochlorite wash for 30 minutes while shaking at 150 r.p.m., and rinsing three times with sterile water. Leaf sections, approximately 1 cm$^2$, were cultured top surface down on coffee callus medium (COF, Table 2). The explants were cultured at 28°–30° C. in the dark or under dim light.

TABLE 2

| COF Media[a] | | | |
|---|---|---|---|
| MS salts[b] | | Sucrose | 40000 |
| B5 vitamins[c] | | | |
| myo-Inositol | 100 | Kinetin | 20 uM |
| Casein hydrolysate | 100 | 2,4-D | 5 uM |
| CE Media[d] | | | |
| MgSO4 7H2O | 300 | Mannitol | 0.5 M |
| Ca(NO3)2 4H2O | 800 | MES | 5 mM |
| NH4H2PO4 | 230 | Cellulysin | 20000 |
| KNO3 | 2000 | Macerase | 5000 |
| NH4Cl | 500 | Pectolyase Y23 | 2500 |
| | | Bovine serum albumin | 1000 |
| EB Media | | | |
| Mannitol | 0.65 M | | |
| MgCl2 | 10 mM | | |
| MES | 5 mM | | |

[a]all media were adjusted to pH 5.6, all quantities in mg/L unless otherwise noted.
[b]Murashige, et al., Physiol. Plant., 15:473, 1962
[c]Gamborg, et al., Exp. Cell Res., 50:151, 1968
[d]the enzyme solution was treated for one hour with 1% neutralized activated charcoal, filter sterilized, and stored frozen.

Production Of Embryogenic suspension Cultures

Proliferating leaf callus was transferred to 50 ml of liquid cell culture media (CM, Table 3) in 250 ml delong flasks and incubated at 27 +/−2° C. on a gyratory shaker at 150 r.p.m. until small white-to-cream colored cells with dense cytoplasm were visible. These small cells were repeatedly subcultured until stable suspensions of small cells were obtained. The cultures have since been maintained on a 7–10 day transfer schedule in 50 mls of CM medium. Six cell lines were produced, one of which, CA-2, was used for the remainder of the experiments reported here.

TABLE 3

| CM Media[a] | | | |
|---|---|---|---|
| Ca(NO$_3$)$_2$4H$_2$O | 800 | Thiamine.HCl | 2.0 |
| MgSO$_4$7H$_2$O | 300 | Nicotinic acid | 1.0 |
| NH$_4$H$_2$PO$_4$ | 230 | p-Aminobenzoic acid | 0.1 |
| KNO$_3$ | 2000 | myo-Inositol | 1010. |
| NH$_4$Cl | 500 | Pyridoxine HCl | 0.5 |
| | | Choline chloride | 5.0 |
| Na$_2$EDTA2H$_2$O | 8.591 | D-Biotin | 0.001 |
| NH$_4$VO$_3$ | 0.023 | Cyanocobalimin | 0.001 |
| CuSO$_4$5H$_2$O | 0.02 | Folic acid | 0.01 |
| NiSO$_4$5H$_2$O | 0.045 | Casein hydrolysate | 100. |
| MnCl$_2$4H$_2$O | 14.7 | Glycine | 2.0 |
| NaMoO$_4$2H$_2$O | 0.388 | Cystine | 1.0 |
| H$_3$BO$_3$ | 2.0 | Methionine | 1.0 |
| ZnSO$_4$7H$_2$O | 1.1 | Adenine sulfate | 40.0 |
| CrK(SO$_4$)$_2$12H$_2$O | 0.098 | Hypoxanthine | 10.0 |
| Na$_2$SeO$_3$ | 0.018 | Thymidine | 10.0 |
| KI | 0.75 | L-Sodium malate | 10.0 |
| Na$_3$Citrate2H$_2$O | 29.4 | Sucrose | 40000 |
| FeSO$_4$7H$_2$O | 29.04 | | |
| | | Kinetin | 10 uM |
| | | 2,4-D | 5 uM |

| CP Media | |
|---|---|
| CM media, with modifications: | |
| plus | |
| Calcium pentothenate | 1.0 |
| minus | |
| Hypoxanthine | |
| Thymidine | |
| L-arabinose | 10.0 |
| new concentration | |
| Galactose | 10.0 |
| Sucrose | 10000 |
| Mannose | 10.0 |
| Rhamnose | 10.0 |
| Trehalose | 10.0 |
| Xylose | 10.0 |
| Glucose | 36000. |
| Mannitol | 54000. |

[a]all media were adjusted to pH 5.6, all quantities in mg/L unless otherwise noted.

Protoplast Isolation and Culture

A 5–7 day post-transfer culture was shaken and allowed to settle for a few seconds before withdrawing a 10 ml aliquot of small cells. The cells were collected by centrifugation for five minutes at 50–100 xg, resuspended in 30 ml of enzyme solution (CE, Table 2), and incubated overnight at 27°–30° C. on a gyratory shaker at 50 r.p.m. Following filtration through a 74 micron mesh stainless steel screen, the protoplasts were harvested by centrifugation, washed with protoplast rinse solution (Ri=CE media, without enzymes and bovine serum albumin), and then centrifuged at 100×g for five minutes over an osmotically-adjusted 41% (v/v) Percoil/R1 cushion. Protoplasts banding above the cushion were collected, rinsed in R1, diluted with a given volume of electropotation buffer (EB, Table 2) or protoplast medium (CP, Table 3), as appropriate, and counted. Protoplasts for electroporation experiments were diluted to a final concentration of 2–4×10$^6$/ml with EB and incubated on ice until used. Protoplasts isolated for regeneration studies were directly diluted to 2×10$^5$ /ml with CP, and thereafter treated as electroporated protoplasts following electroporation (see, Example 3), except that kanamycin sulfate (kanamycin) was omitted from the media. Values of 10–30×10$^6$ CA-2 protoplasts per 10 ml aliquot were routinely obtained.

Following transient expression electroporation experiments, the protoplasts were diluted to 2×10$^5$/ml with CP and cultured in the dark at 28° C. for 2 to 3 days before being assayed. For stable transformation experiments, the protoplasts were diluted 1:1 with CP four days after electropotation, and again three weeks later with CM plus kanamycin (100 mg/L). The cultures were maintained as for suspension cultures, except for the addition of continuous kanamycin selection.

EXAMPLE 2

Plant Regeneration Through Induction of Coffea Somatic Embryos

Embryogenesis was pre-induced by transferring CA-2 cells to a medium composed of MS salts (without hormones), B$_5$ vitamins, and 3% sucrose. Full induction was accomplished by transferring to liquid induction medium (LIM—0.5×MS major salts with KNO$_3$ increased to 38 mM, B$_5$ vitamins, and 2% sucrose), and then to LIM plus 0.8% Difco Noble agar. Single embryos were then dissected out of the resulting embryo clusters and subcultured on the same medium. Embryos that germinated and formed a root were transferred to GA-7 containers (Magenta Corp.) containing sterile vermiculite moistened with Hoagland's solution (Boagland and Arnon, Calif. Agric. Exp. Stn. Circ., 347:1, 1950) for the formation of plants. After a period of acclimation, the plants were transferred to soil and grown in a growth chamber (28° C., 12 hours/day photoperiod).

EXAMPLE 3

Transformation of Protoplasts

Determination of Coffea Stable Transformation Conditions

Optimal conditions for electropotation of Coffea protoplasts were determined by first establishing the electroporation conditions for transient expression and stable transformation in protoplasts from tobacco leaf and suspension cell cutures and tomato leaves, and applying these data to CA-2 protoplasts. Electroporation was performed using a modification of the protocol developed by Fromm (From, et al., Proc. Natl. Acad. Sci. U.S.A. 82:5824, 1985; From, et al., Nature, 319:791, 1986). 2–4×10$^6$ protoplasts in 1 ml EB, plus or minus DNA, were incubated for 10–12 minutes in an ice-cooled disposable 0.4×1 cm plastic cuvette to which aluminum heat duct tape (3M) had been attached to the 0.4 cm internal lateral surfaces as electrodes. Electroporation was achieved by discharging a 330 volt×350 microfarad capacitor across the electrodes. (Final resistance=800–1050 ohms; RC =215–250 milliseconds). DNAs used were 20–40 μg/ml of either Hind III digested plasmid pGA472 (An, et ai., EMBO Journal 4(2):277, 1958 ), for producing kanamycin resistant stable transformants, or closed-circular pUCS-CaMV-CAT ( a derivative of pCaMVCAT (From, et al., Proc. Natl. Acad. Sci. U.S.A., 82:5824, 1985)), for transient expression experiments. 20–40 μg/ml of sterile calf thymus DNA (Sigma) or linearized pSh2-109 (a partial maize Shrunken-2 gene) (Barton, et al., in Regulation of Carbon and Nitrogen Reduction and Utilization in Maize, American Society of Plant Physiologists, Rockville, Md., 363, 1986 ) cloned into pTZ19U (Mead, et al., Nuc. Acids Res., 13. (4):1103, 1985) ) were included as carrier DNA in all experiments. Following electroporation, the protoplasts were incubated on ice for 10–20 minutes and cultured as described above.

Plasmid DNAs were purified via CsCl/ethidium bromide centrifugation (Zarowitz, Ph.D. Dissertation, University of Missouri, Columbia, 1983; Birnboim, et al., Nucleic Acids Research, 7:1513, 1979). Following standard cleanup protocols, the DNAs were sterilized with 70% ethanol and resuspended in sterile water.

The electroporated protoplasts were incubated for 2-3 days, assayed for chloramphenicol acetyltransferase (CAT) activity (From, et al., Proc. Natl. Acad. Sci. USA, 82:5824, 1985) using $^{14}$C-Chlorampnenlcol (60 mCi/mmole, New England Nuclear), and the relative abundance of the acetylated chloramphenicol spots noted.

Transient expression of the CAT gene in tobacco and tomato protoplasts is observed with one pulse of 160-170 volts/cm, and increases with increasing applied voltage (one pulse) up to approximately 230 volts/cm. The level of expression then remains constant up to 270-280 volts/cm, above which the intensity of the spots associated with the acetylated chloramphenicols drops dramatically. Observations of the physical integrity, cell wall formation, and ability to divide of the treated protoplasts revealed that the high expression plateau is correlated with the protoplasts' inability to divide, while the sharp drop-off of expression is associated with the physical disruption of the protoplasts during the electroporation event. It is believed that voltages producing the high expression plateau render the cells unable to divide but otherwise capable of synthesizing the CAT enzyme molecule. Due to the stability of the CAT enzyme, these protoplasts now display high levels of CAT activity.

Stable transformation experiments were then performed to determine the number of kanamycin-resistant calli (tomato and tobacco) and/or plantlets (tobacco) produced at each voltage. Kanamycin resistance is produced by the expression of the gene for neomycin phosphotransferase-II (NPT-II). The relationship between the minimum voltage required for maximal transient expression (Vmt) and stable transformation (Vms) for tobacco and tomato protoplasts was calculated, the Vmt for Coffea protoplasts experimentally derived, and the Coffea Vms predicted by applying the empirical Vmt - Vms differential for tobacco and tomato protoplasts to the Coffea Vmt.

Ensuing stable transformation experiments yielded transformed kanamycin-resistant tobacco/tomato calli across a voltage range of 160-190 volts/cm in the presence of pGA472. No stable transformants were obtained using voltages in the plateau of high expression or with "no DNA" controls. From these results, the Vmt and Vms for both tobacco and tomato protoplasts were taken to be 230 volts/cm and 170-190 volts/cm, respectively. Analogous transient expression experiments with CA-2 protoplasts yielded a Vmt of about 240 volts/cm. The voltage effects on CA-2 protoplasts were similar to those observed with tobacco and tomato protoplasts. Therefore, stable electroporation of CA-2 protoplasts was predicted to occur at about 190-200 volts/cm.

CA-2 protoplasts were electroporated over a range of 150-240 volts/cm. After 3-4 months of kanamycin selection, very small cell clumps were observed in samples CA477-2 and CA477-3/4, corresponding to treatment voltages of 220 and 200 volts/cm, respectively. After another three months enough material was available from CA477-2 to induce embryogenesis and to test for the presence of the pGA472 NPT-II gene construct. CA477-3/4 required an additional two months of culturing. Kanamycin-resistant tissue was not obtained from any "no DNA" controls. While the specific transformation rate is unknown, it was estimated that Coffea transformation was about $1 \times 10^{-6}$ per electroporated protoplast. Stable electroporative transformation of tobacco (selection performed on solid medium) was as high as $1 \times 10^{-4}$ per electroporated protoplast.

Molecular Analysis of Plant Tissue

Twenty µg of DNA obtained from frozen CA-2 cell suspension tissue (Della-porta, et al., in Molecular Biology of Plants—Laboratory Manual, Cold Spring Harbor Laboratory, Cold Spring Harbor, N.Y., pg. 35–36, 1984) were digested with various restriction enzymes and processed for Southern analysis (Maniatis, et al., in Molecular Cloning A Laboratory Manual, Cold Spring Harbor Laboratory, Cold Spring Harbor, New York. pp. 382-389, 1982) with a $^{32}$P-radiolabelled (Feinberg et al., Analytical Biochemistry, 132:6-13, 1983) 1.2 kbp Barn HI x Bind III NPT-II gene restriction fragment probe from pPK65 (Koziel, et al., J. Molecular and Applied Genetics, 2:549, 1984). Similarly digested pGA472 DNA and DNA from untransformed Coffea plant tissues were used as positive and negative control DNAs, respectively.

Southern Analysis of Kanamycin-Resistant Coffea Tissue

Southern analysis of CA477-2 DNA was performed as described herein. No hybridization of the kanamycin probe to the untransformed control DNA was observed. Pst I×Sst II×Hind III digested CA477-2 DNA produces major bands of 1.8 kbp and 400 bp, and one =2.8 kbp minor band of hybridization to the NPT-II gene probe. The 400 bp fragment represents the promoter and 5' portion of the NPT-II gene, while the 1.8 kbp band, based upon its size and high signal strength, must arise from concatemers of the input construct (Hind III-digested pGA472). The 2.8 kbp band is likely the signal from a fusion fragment arising from the loss of the pGA472 Hind III site during insertion into the plant chromosome. CA477-3/4 produces three bands of hybridization to the NPT-II gene probe: the 400 bp promoter-5' fragment, and 1.6 and 5.5 kbp bands. The latter two bands again probably represent fusion fragments, with the 1.6 kbp fragment also undergoing a loss of approximately 200 bp of pGA472 sequence upon insertion. However, according to the published map of pGA472 (An, EMBO Journal, 4(2):277, 1985), the 1.6 kbp fragment is still of sufficient length to produce an intact NPT-II gene. That these signals are from the pGA472 NPT-II gene is supported by the results of the Southern analysis of Bam HI×Hind III digests of CA477-2 and CA477-3/4 DNA. The 400 bp signal disappeared with these digests, and all other bands increased in size by the expected 200 bp.

The ability of Hind III to release native full length molecules of pGA472 from CA472-2 strongly indicates the presence of concatemers, and therefore, multiple copies of pGA472. Preliminary reconstruction experiments suggest 5-10 copies of pGA472 per haploid CA477-2 genome. Similarly, it appears there are two types of pGA472 insertions in CA477-3/4 present at 1-2 copies of pGA472 per haploid Coffea genome. The fact that CA477-2 cultures grow faster under kanamycin selection than those of CA477-3/4, is consistent with the former having a higher NPT-II copy number. The presence of the partially deleted 1.6 kpb band in CA477-3/4 is consistent with the DNA rearrangements observed with electroporation-mediated transformation (From, et ai., Nature, 319:791-793, 1986).

EXAMPLE 4

Characterization of Embryogenic Cell Line and Protoplasts

The *C. arabica* leaf suspension cell line, CA-2, is composed of small (20–30 micron diameter), cytoplasmically dense cells. Usually five or more transfers to induction media (LIM) are required for a high rate of embryogenesis. After the first few transfers to LIM, large brown cell clusters form which give rise to a friable tissue which, in turn, produces white globular embryogenesis structures. In liquid, the friable tissue sluffs from the globular structures and the large cell clumps are transferred to LIM agar plates. More than 50 somatic embryos can arise from a single callus mass, however, the embryos should be separated from the surrounding callus for further development. Many of the somatic embryos develop into normal plants, but some embryos fuse together or develop one or three cotyledons. The pattern of development generally follows the high frequency somatic embryogenesis (HFSE) mode previously described (Sondahl, et al., L. Z. Pflanzenphysiol. Bd., 81S:395, 1977; Sondahl, et al., in Tissue Culture and Its Application, T. Thrope, ed., Academic Press, New York, pp. 325–358, 1981; Sondahl, et al., in Handbook of Plant Cell Culture, Vol. 3., Ammirato, et ai., eds., Macmillan, New York, pp. 564–590, 1984).

The freshly isolated CA-2 protoplasts assume an oval shape within 24 hours and quickly undergo cell wall formation. Cell division is observed within 4–6 days following protoplast isolation, and cell clusters are visible to the unaided eye after two weeks of culture. Within one month of protoplast isolation the culture strongly resembles the progenitor cell line and can be induced to form somatic embryos. Electroporated protoplasts develop in a manner similar to non-electroporated protoplasts without any delay in cell regeneration or colony formation.

Most of the protoplasts in the stable transformation experiments die soon after transfer to media containing kanamycin. However, a few cell clumps appeared in two of the treatments after several months of continuous kanamycin selection. After several more transfers to fresh medium containing kanamycin, the two positive treatments yielded suspension cultures similar in appearance to CA-2. These two established transformed cell lines, CA477-2 and CA477-3/4, are now maintained under the same protocol as CA-2 in regards to culture media (with the addition of kanamycin), transfer schedule, and transfer inoculum. Both CA477-2 and CA477-3/4 have required more transfers to induction medium than earlier protoplast regeneration experiments. These cultures, in the presence of constant kanamycin selection (100 mg/L), have regenerated embryos, some of which have germinated to produce cotyledons.

The present invention is not to be limited in scope by the Examples which are intended as illustrations of one aspect of the invention and any Coffea plants, protoplasts, cell lines, or seeds which are functionally equivalent are within the scope of this invention. Indeed, various modifications of the invention in addition to those shown and described herein will become apparent to those skilled in the art from the foregoing description and accompanying figures. Such modifications are intended to fall within the scope of the appended claims.

What is claimed is:

1. An isolated cell derived from a protoplast of the species *Coffea arabica* wherein the protoplast is derived from a cell line having all of the identifying characteristics of cell line CA-2 and is genetically transformed by means selected from the group consisting of electroporation and protoplast fusion to possess a stable trait wherein the cell can be maintained in cell culture and regenerated to a plantlet having the stable trait.

2. A cell of claim 1 wherein the cell is transformed with foreign DNA.

3. The cell of claim 2 wherein the DNA is from a species of the species *Coffea arabica* which is different from the species of *Coffea arabica* of the cell.

4. The cell of claim 1 wherein the cell is transformed with DNA from a different plant variety than the plant variety of the cell.

5. The cell of claim 1 wherein the cell is transformed with DNA from the same plant variety as the plant variety of the cell.

6. The cell as in either of claim 4 or 5, wherein the transformation DNA includes a marker gene.

7. A cell derived from a protoplast of the species *Coffea arabica* wherein the protoplast is derived from a cell line having all of the identifying characteristics of cell line CA-2 and is genetically engineered to possess a stable trait and the cell can be maintained in cell culture and become a plantlet having the stable trait wherein the cell is obtained by:
  a) culturing *Coffea arabica* explant tissue to produce a callus,
  b) isolating a cell suspension comprising small cytoplasmically dense embryogenic cells from the callus,
  c) treating the cell suspension to obtain protoplasts,
  d) transforming the protoplasts, and
  e) regenerating cells from the transformed protoplasts.

8. The cell of claim 7, where in step d), the protoplasts are transformed using electroporation.

* * * * *